(12) United States Patent
Hecker et al.

(10) Patent No.: US 7,524,949 B2
(45) Date of Patent: Apr. 28, 2009

(54) DOUBLE STRANDED DNA INHIBITOR OF IRF-1 ACTIVITY

(75) Inventors: Markus Hecker, Göttingen (DE); Andreas H. Wagner, Göttingen (DE)

(73) Assignee: Avontec GmbH, Gottingen (DE)

( * ) Notice: Subject to any disclaimer, the term of this patent is extended or adjusted under 35 U.S.C. 154(b) by 761 days.

(21) Appl. No.: 10/398,592

(22) PCT Filed: Oct. 4, 2001

(86) PCT No.: PCT/DE01/03835

§ 371 (c)(1), (2), (4) Date: Oct. 2, 2003

(87) PCT Pub. No.: WO02/29044

PCT Pub. Date: Apr. 11, 2002

(65) Prior Publication Data

US 2004/0048820 A1    Mar. 11, 2004

(30) Foreign Application Priority Data

Oct. 4, 2001   (EP)   ................. PCT/DE01/03835

(51) Int. Cl.
C07H 21/04 (2006.01)
A61K 31/70 (2006.01)
(52) U.S. Cl. ................... 536/24.5; 536/23.1; 514/44
(58) Field of Classification Search ............ None
See application file for complete search history.

(56) References Cited

U.S. PATENT DOCUMENTS 6,060,310 A * 5/2000 Cho-Chung ............ 435/375

FOREIGN PATENT DOCUMENTS

| JP | 9227413 | 2/1996 |
|---|---|---|
| WO | WO 00/06769 | 2/2000 |
| WO | WO 00/09525 | 2/2000 |
| WO | WO 00/44407 | 2/2000 |
| WO | WO 00/62736 | 3/2000 |
| WO | WO 00/61729 | 4/2000 |

OTHER PUBLICATIONS

Tnani et al. Biochimica et Biophysica Acta 1999, vol. 1451, pp. 59-72.*
Hecker et al. British Journal of Pharmacology 1996, vol. 118, pp. 2178-2184.*
Tanaka et al. Molecular and Cellular Biology 1993, vol. 13, pp. 4531-4538.*
Amoa-Apraku eet al., "A non-nucleotide-bridged DNA decoy inhibits renal epithelial nitric oxide synthase expression," *Chemical Abstracts*, 133(17):46, 2000.
Amoah-Apraku et al., "A non-nucleotide-bridge DNA decoy inhibits renal epithelial nitric oxide synthase expression," *Kidney International*, 57(1):83-91, 2000.
GenBank Accession No. L05078, Jan. 6, 1995.
GenBank Accession No. NM002198, Oct. 4, 2003.
GenBank Accession No. X14454, Sep. 5, 1996.
Horiuchi et al., "Interferon regulatory factor-1 up-refulates angiotensin II type 2 receptor and induces apoptosis," *Chemical Abstracts*, 127(1):474, 1997.
Horiuchi et al., "The growth-dependent expression of angiotensin II type 2 receptor is regulated by transcription factors interferon regulatory factor-1 and -2," *Chemical Abstracts*, 123:220, 1995.
Krzesz et al., "Cytokine-inducible CD40 gene expression in vascular smooth muscle cells is mediated by nuclear factor kappaB and signal transducer and activation of transcription-1," *FEBS Lett.*, 453:191-196, 1999.
Sato et al., "Inhibition of interferon regulatory factor-1 expression results in predominance of cell growth stimulatory effects of interferon-gamma due to phosphorylation of Stat1 and Stat3," *Blood*, 90(12):4749-4758, 1997.
Uwe et al., "Tumor necrosis factor α induces a metalloprotease disintegrin, ADAM8 (CD 156): implications for neuron-glia interactions during neurodegeneration," *Chemical Abstracts*, 134(5):589, 2001.
Wagner et al., "Cytokine-inducible CD40 expression in human endothelial cells is mediated by interferon regulatory factor-1," *Blood*, 99(2):520-525, 2002.

* cited by examiner

Primary Examiner—Tracy Vivlemore
(74) Attorney, Agent, or Firm—Fulbright & Jaworski, LLP

(57) ABSTRACT

The present invention refers to inhibitors of the transcription factors IRF-1, their use as therapeutic agents as well as their use for prevention and therapy of cardiovascular complications like re-stenosis after percutaneous angioplasty or stenosis of venous bypasses, chronic (transplant arteriosclerosis or vasculopathy) or acute transplant rejection, graft versus host disease (GVHD), immunological hypersensitivity reactions (allergies), particularly bronchial asthma and atopic dermatitis, chronic recurrent inflammatory diseases, particularly ulcerative colitis and Crohn's disease, psoriasis and sarcoidosis, as well as autoimmune diseases, particularly diabetes mellitus, multiple sclerosis, collagenoses (e. g. systemic lupus erythematodes), rheumatoid arthritis and vasculotids.

2 Claims, 9 Drawing Sheets

DOUBLE STRANDED DNA INHIBITOR OF IRF-1 ACTIVITY

This application claims priority to PCT/DE 01/03835, filed on Oct. 4, 2001, DE 100 49 549.4 flied Oct. 6, 2000 and DE 100 59 144.2, filed on Nov. 29, 2000. The entire content of these applications are incorporated by reference.

The present invention refers to inhibitors of the transcription factors IRF-1, their use as therapeutic agents as well as their use for prevention and therapy of cardiovascular complications like re-stenosis after percutaneous angioplasty or stenosis of venous bypasses, chronic (transplant arteriosclerosis or vasculopathy) or acute transplant rejection, graft versus host disease (GVHD), immunological hypersensitivity reactions (allergies), particularly bronchial asthma and atopic dermatitis, chronic recurrent inflammatory diseases, particularly ulcerative colitis and Crohn's disease, psoriasis and sarcoidosis, as well as autoimmune diseases, particularly diabetes mellitus, multiple sclerosis, collagenoses (e.g. systemic lupus erythematodes), rheumatoid arthritis and vasculotids.

The endothelium of blood vessels plays a key role in inflammatory diseases because it represents the primary interaction site for circulating inflammation competent cells with the tissue. In acute or chronic inflammation manifold interactions between endothelium cells and both monocytes and polymorphonuclear neutrophil granulocytes are described. Recently the interaction between endothelium cells and pro-inflammatory T helper cells (TH1) in autoimmune diseases (e. g. rheumatoid arthritis), arteriosclerotic lesions of blood vessels walls including transplant and venous bypass vasculopathy as well as re-stenosis after percutaneous angioplasty and in chronic recurrent inflammatory diseases (e. g. Crohn's disease, psoriasis) are increasingly discussed. Lymphocytes and endothelium cells communicate over the CD40/CD154 receptor/ligand system (also known as TNF receptor/ligand-5-system) with consecutive increase of expression of chemokine and adhesion molecules in the endothelium. Moreover, endothelium cells in contrast to other antigen presenting cells like monocytes seem to release biological active interleukin 12 solely after activation of the CD40 signalling pathway in an amount similar to maximally stimulated monocytes (these are generally thought to be the main source of interleukin 12). Interleukin 12 is the primary stimulus and differentiation factor, respectively, for naive T helper cells which react with an increased production of interferon γ and expression of CD154, respectively, on their surface (these T helper cells are then regarded as TH1 cells). Interferon γ in turn increases the expression of CD40 in endothelium cells resulting in a vicious cycle in which endothelium cells, T- helper cells and recruited monocytes stimulate each other and keep the inflammatory reaction going.

The co-stimulating properties of CD40/CD154 which trigger the inflammation have been demonstrated in animal models for diseases including Crohn's disease and acute or chronic transplant rejection (vasculopathy). Not only the endothelium leukocyte interaction via CD40/CD154 plays a role here, but also for example the CD40/CD154-mediated interaction of monocytes/macrophages or dendritic cells with TH1-cells and naive T helper cells, respectively. Further CD40 may e.g. be expressed by smooth muscle cells in the vessel lining and also by keratinocytes in skin or synovial fibroblasts in joints. Activation of the CD40 pathway in these cells is furthermore not only of importance for inflammatory reactions, but also leads to rebuilding processes in tissue as for example remodelling of vessel lining in transplant vasculopathy, skin changes in psoriasis or erosions of joint cartilage in rheumatoid arthritis. Beside CD154 induced, interleukin 12 depend and TH1 mediated chronic inflammatory diseases and autoimmune reactions, respectively, including Diabetes mellitus, multiple sclerosis, sarcoidosis and vasculotids the co-stimulatory properties of CD40/CD154 are also important for differentiation of B-lymphocytes in antibody producing plasma cells which is triggered by contact with TH2-cells. Thereby B-lymphocytes express CD40 and TH2-cells express CD154. Without this co-stimulation plasma cells produce primarily antibodies of the IgM type and barely antibodies of type IgE or IgG. An exaggerated TH2 response, i. e. excessive production of type IgE or IgG antibodies plays an important role in mainly allergy caused chronic recurrent inflammatory diseases as bronchial asthma, atopic dermatitis and ulcerative colitis but also in collagenoses as systemic lupus erythematodes (SLE), in which the production of auto reactive auto antibodies is of special importance and which is therefore regarded as a generalized autoimmune disease. In general differentiation between autoimmune diseases and chronic recurrent inflammatory diseases is problematic because a common predisposing factor seems to be the imbalance between TH1 and TH2 mediated cellular and humeral immune reaction, respectively.

Presently the only useful therapeutic approach for the treatment of diseases inter alia associated with the CD40/CD154 signalling pathway—apart from blocking antibodies against CD 154—is the inhibition of CD40 expression in CD154 target cells. One of the drawbacks of the treatment with anti-CD154-antibodies is the risk of hypersensitivity reactions (against the antibody), particularly with repeated application, and the poor accessibility of at least tissue-based epitopes (e. g. infiltrated T-lymphocytes) because antibodies must be applied into the blood. However, as for many other cytokine receptors, too, there are no small molecular receptor antagonists for CD40. Due to trimerization of the receptor molecules after ligand binding CD40 antibodies tend to activate CD154 target cells. Other strategies delimiting from the commonly decay of the inflammatory reactions consist of the stimulation of the TH1 cell response at the preponderance of the TH2 cell response (e.g. by administering of a TH1 cytokine like interferon γ) or vice versa by stimulation of the TH2 cell response at the preponderance of the TH1 cell response (e.g. by administering of a TH2 cytokine like interleukin-10). Because the T helper cell reactions cancel out each other by means of cytokine mediation (i.e. the preponderance of the TH1 cell response leads to a decay of the TH2 cell response and vice versa) these strategies hold the danger to disinhibit the respective other pathway of the T helper cell response. This may in turn leads to the possibility of the respective other inflammatory reaction.

Thus, one problem of the present invention is the provision of agents for prevention and/or therapy of inflammation diseases, which among others are associated with the CD40/CD154 co-stimulation.

The problem is solved by the subject matter defined in the claims.

The invention is illustrated by the following figures.

FIG. 1 shows graphically the result of the CD40 mRNA expression (RT-PCR analysis) in not-stimulated TNFα (1000 U/ml), IFNγ (1000 U/ml) and TNFα (100 U/ml) plus IFNγ (1000 U/ml)-stimulated cultivated human endothelium cells after 9 hours (% related to the basal CD40 expression in not-stimulated endothelium cells) (n=5-9, *P<0.05 versus basal, †P<0.05 versus TNFα and IFNγ).

FIG. 2 shows schematically the result of the time dependent increase of the nuclear translocation of NFκB (p65/p50 heterodimer) of the p91/p91 homodimers of STAT-1 and of IRF-1 in human endothelium cells, incubated for 0.5 hours (NFκB and STAT-1) and. 3 hours (IRF-1) with TNFα (1000 U/ml), respectively, IFNγ (1000 U/ml) and TNFα (100 U/ml) plus IFNγ (1000 U/ml). A pre-incubation (1 hour) with cycloheximide (Cx, 1 μM) demonstrates, that IRF-1 is expressed de novo. Representative electrophoretic mobility shift analysis, comparable results were obtained in further experiments.

FIG. 3 shows schematically the results of specific effects of Cis-element decoys against STAT-1 NFκB and IRF-1 (10 μM, 4 h pre-incubation) on (a) the mRNA level of CD40 (n=3-5, statistical summary, in % related to the maximum value, *P<0.05 versus TNFα/IFNγ), (b) the mRNA-level of CD40 and E-selectine (representative RT-PCR-analysis, comparable results were obtained in further experiments), (c) the CD40 protein level (representative western blot, comparable results were obtained in further experiments, in human endothelium cells which were incubated for 9 hours (RT-PCR analysis) and 24 hours (western blot), respectively, with TNFα (100 U/ml)/IFNγ (1000 U/ml). In the experiments shown under (b) and (c) the relative intensities (%) determined by densitometrical analysis (One-Dscan-Gel Analysis Software, Scanalytics, Billerica, Mass., USA) are shown in relation to the maximum values at cytokine stimulation.

FIG. 4 shows schematically the effects of different Cis-element decoys against STAT-1, NFκB and IRF-1 (10 μM, 4 h pre-incubation) on the CD40 protein level (a) determined via Fluorescence Activated Cell Sorting (FACS) in human endothelium cells which were incubated for 24 hours with TFNα (100 U/ml)/IFNγ (1000 U/ml) and (b) the assay for the cell surface protein PECAM-1 characteristic for endothelial cells. An overlay of the original measurement of the IgG isotypecontrol and from TNFα/IFNγ treated (CD40) and non stimulated (PECAM-1) cells, respectively is shown in (a) and (b) each as well as the logarithmic values of the respective average fluorescence intensities in a table. Representative experiment, comparable results were obtained in further experiments.

Figure 1:
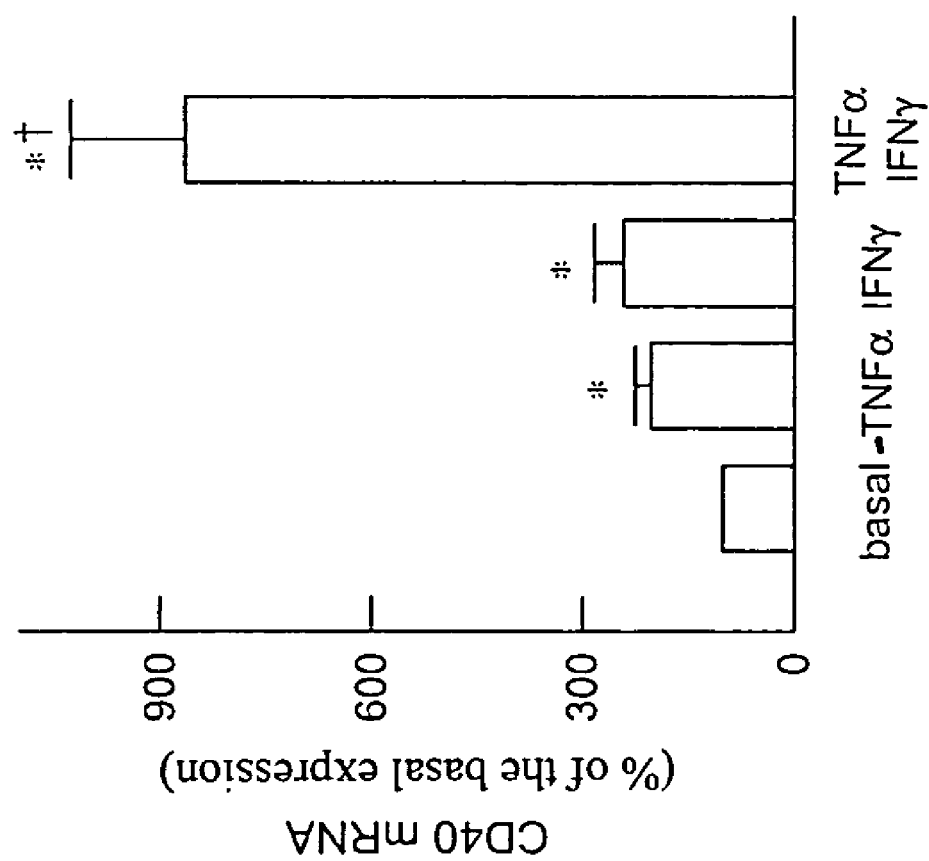
Figure 2:
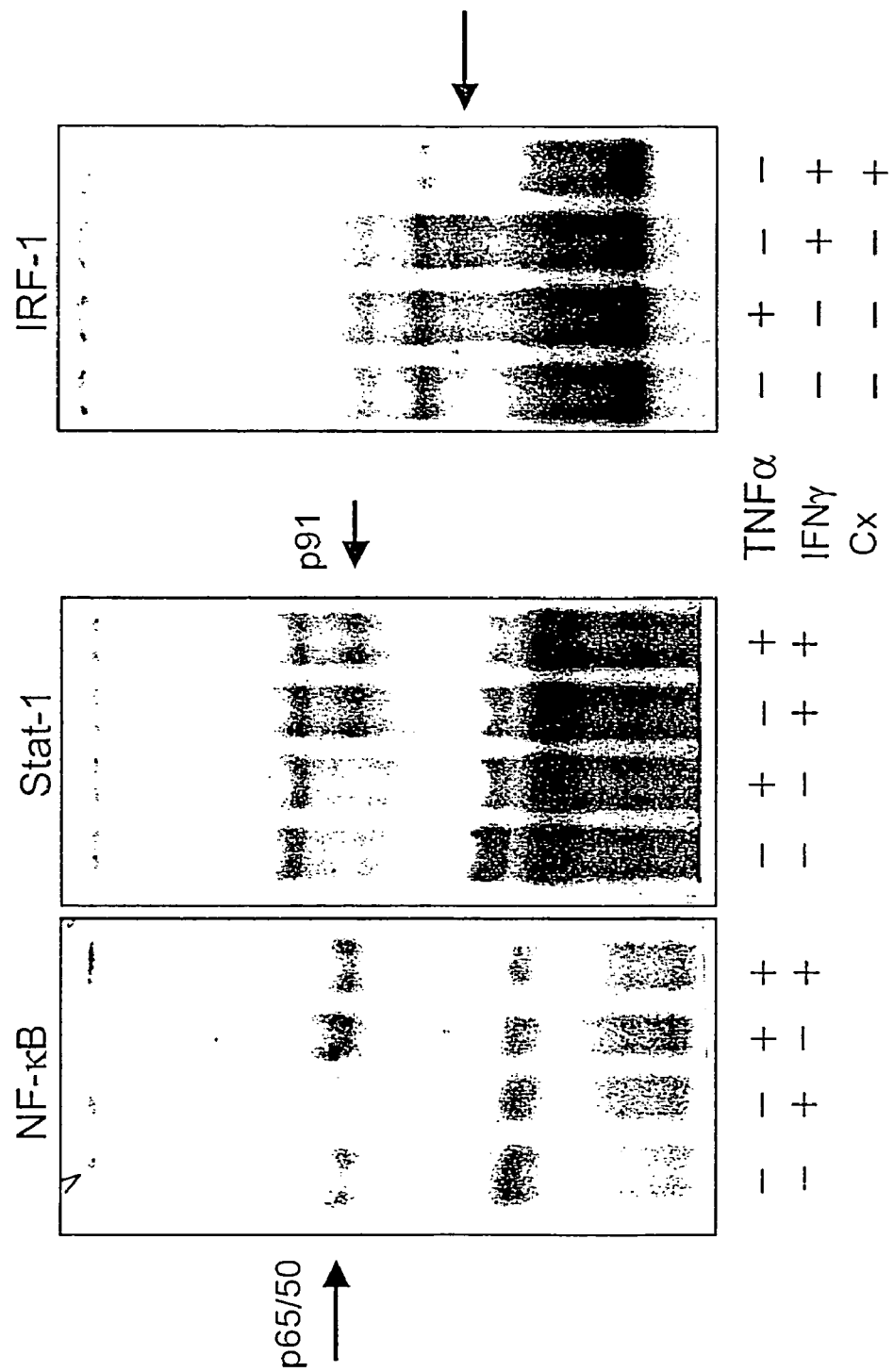
Figure 3:
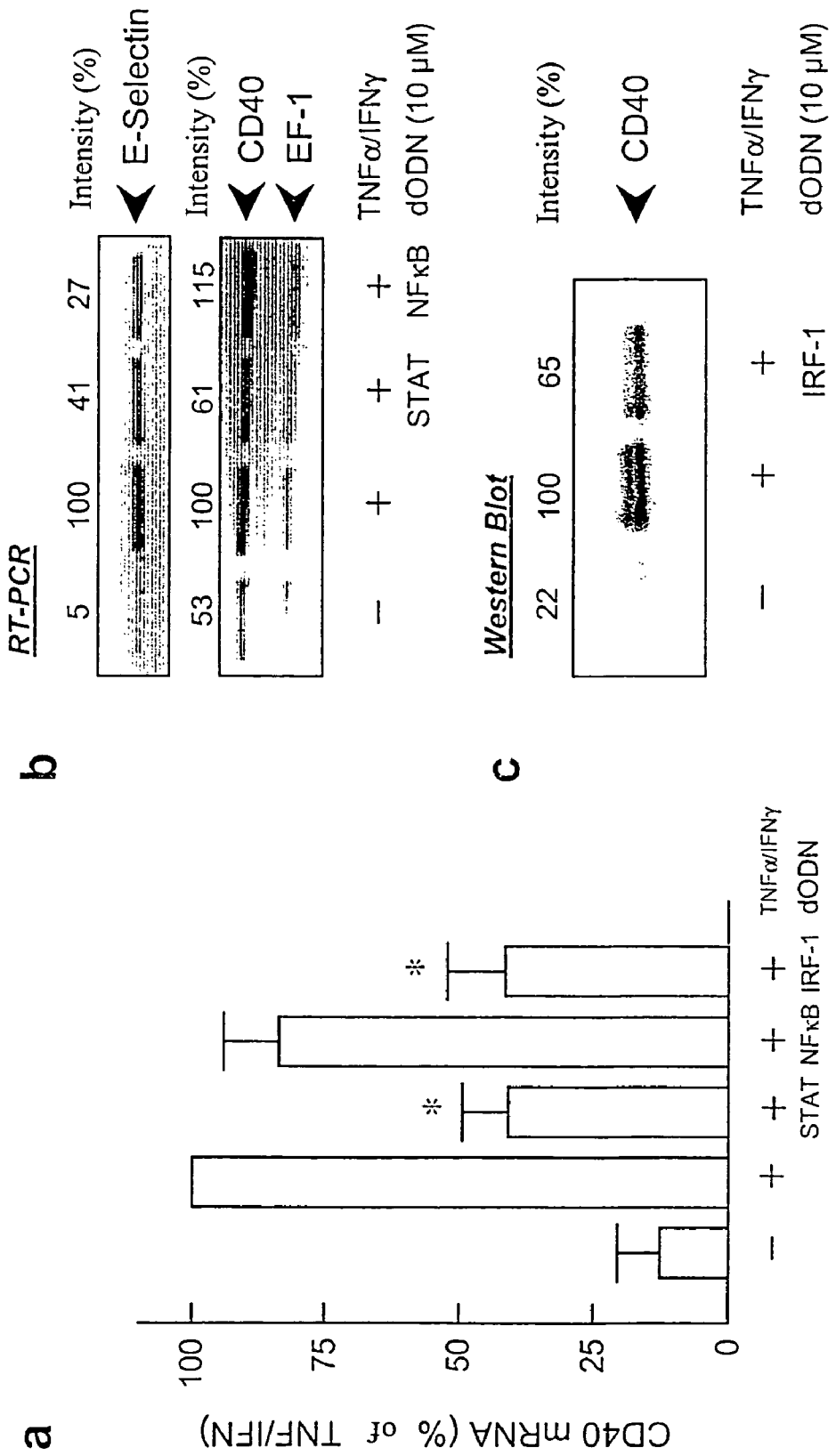
Figure 4:
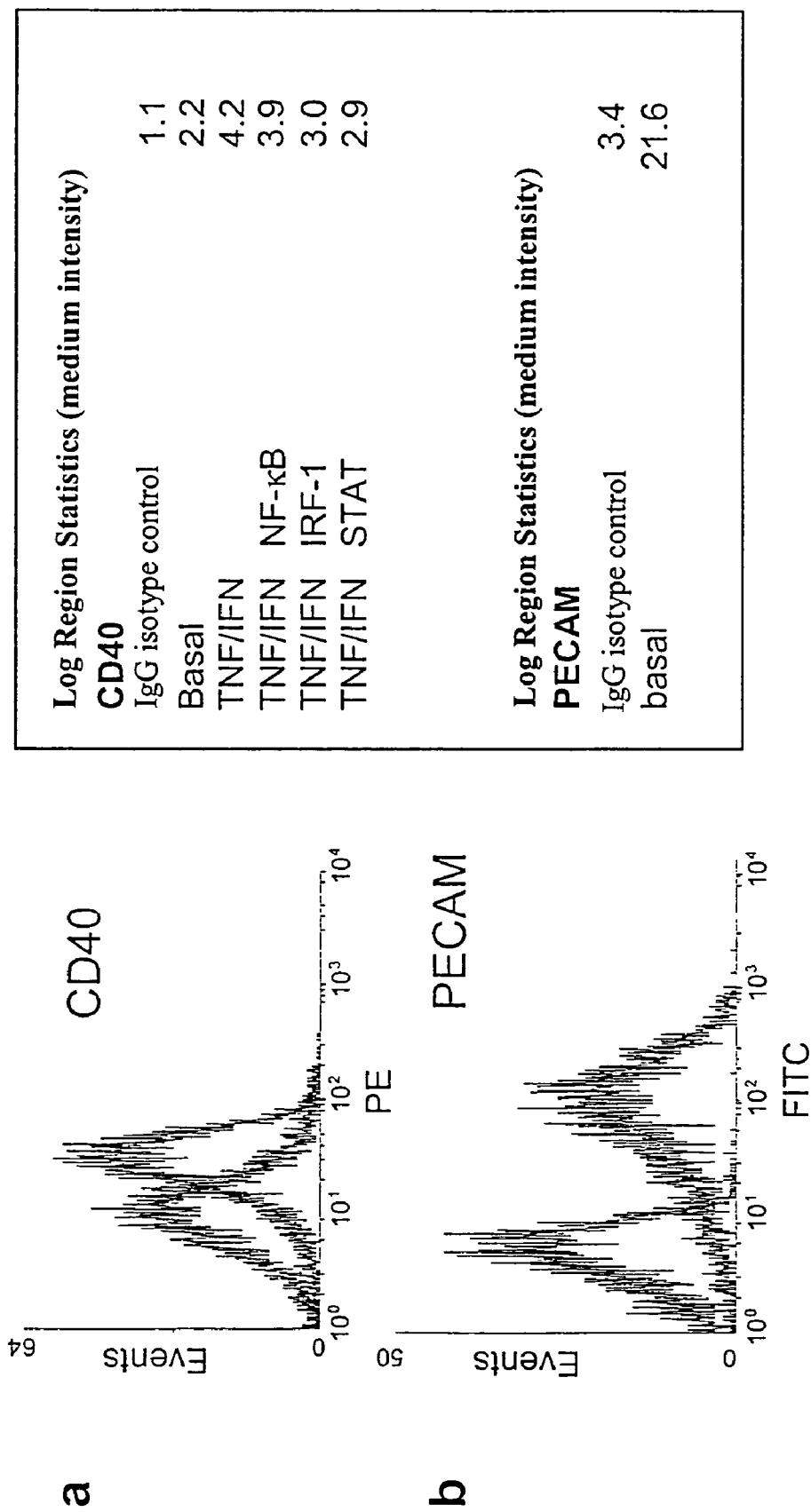
Figure 5:
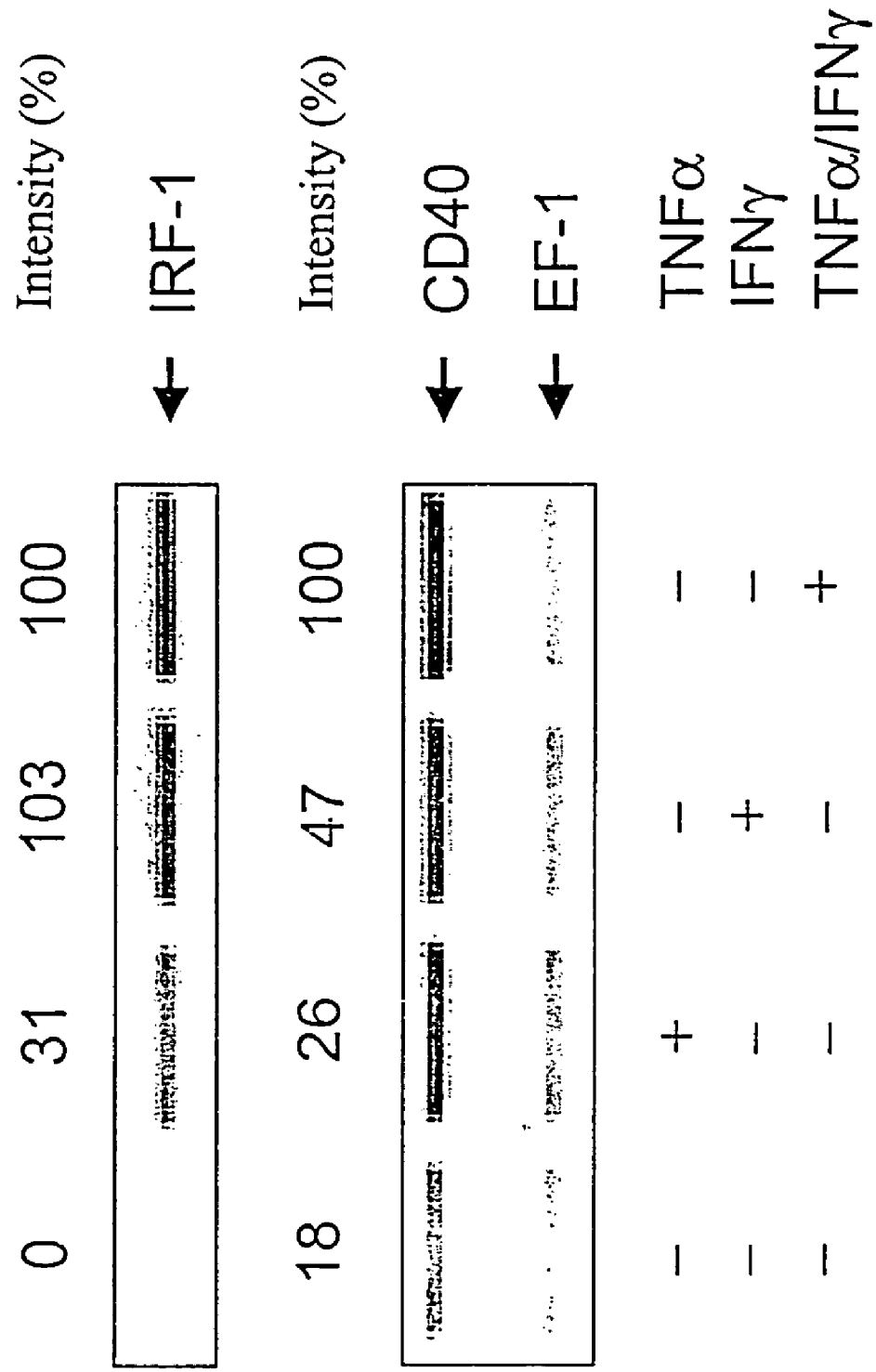
FIG. 5 shows schematically the results of the effects of TNFα (2000 U/ml, IFNγ (1000 U/ml) and TNFα/100 U/ml) plus IFNγ (1000 U/ml) on the CD40 and IRF-1 mRNA level, respectively, in human endothelium cells after 9 hours incubation. Representative experiment, comparable results were obtained in further experiments.
Figure 6:
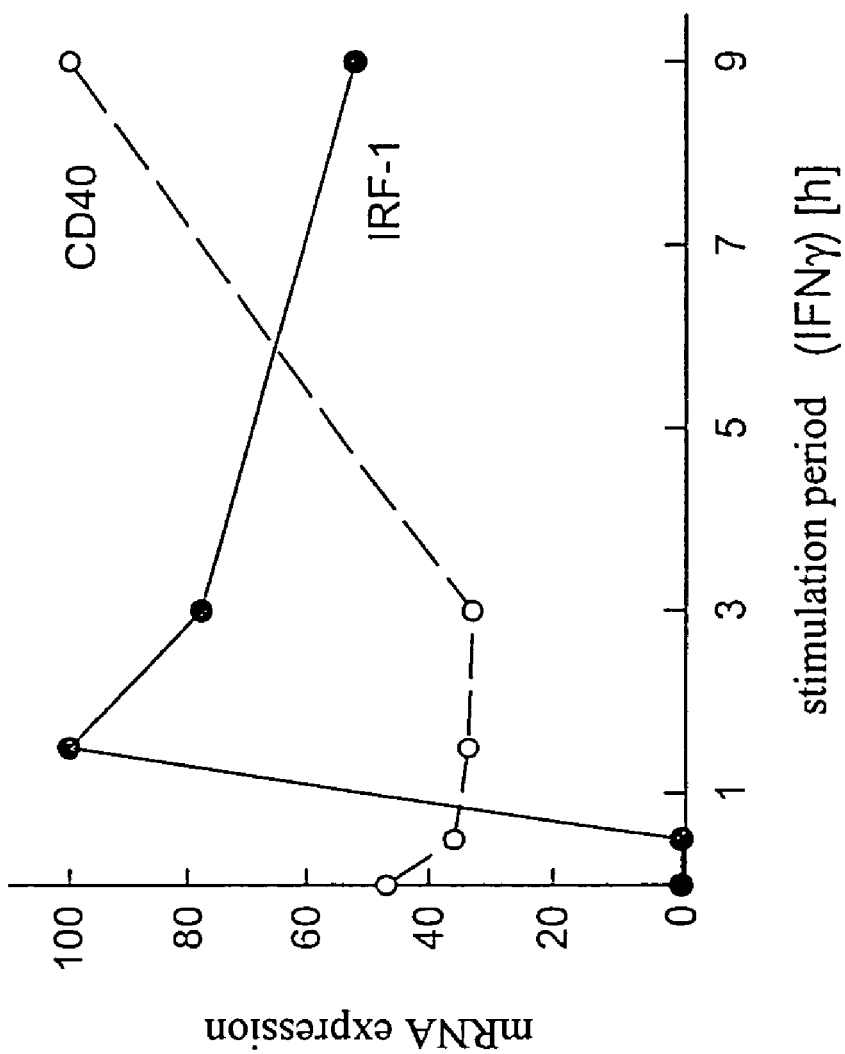
FIG. 6 shows schematically the results of the time dependant increase of the CD40 and IRF-1 mRNA expression, respectively, in human endothelium cells, which were incubated for 0, 0,5, 1,5, 3 and 9 hours with IFNγ (1000 U/ml). Representative experiment, comparable results were obtained in further experiments.
Figure 7:
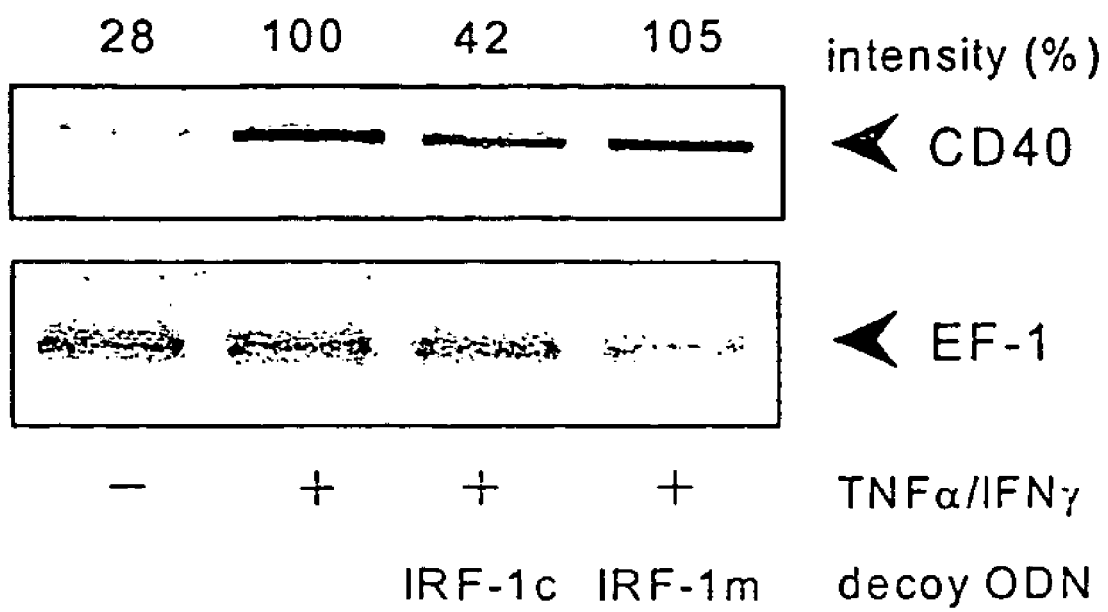

FIG. 7 shows schematically the specificity of the Cis-element decoy effect on the CD40 mRNA expression in human endothelium cells. The pre-incubation (4 hours) with the Cis-element decoy (IRF-1n, cons, 10 μM), but not the pre-incubation with the respective mutated control oligonucleotide (IRF-1n mut, 10 μM) inhibits the CD40 mRNA expression in cells which were subsequently incubated with TNFα (100 U/ml) and IFNγ (1000 U/ml) for 9 hours. Representative RT-PCR analysis, comparable results were obtained in further experiments.

Figure 8:
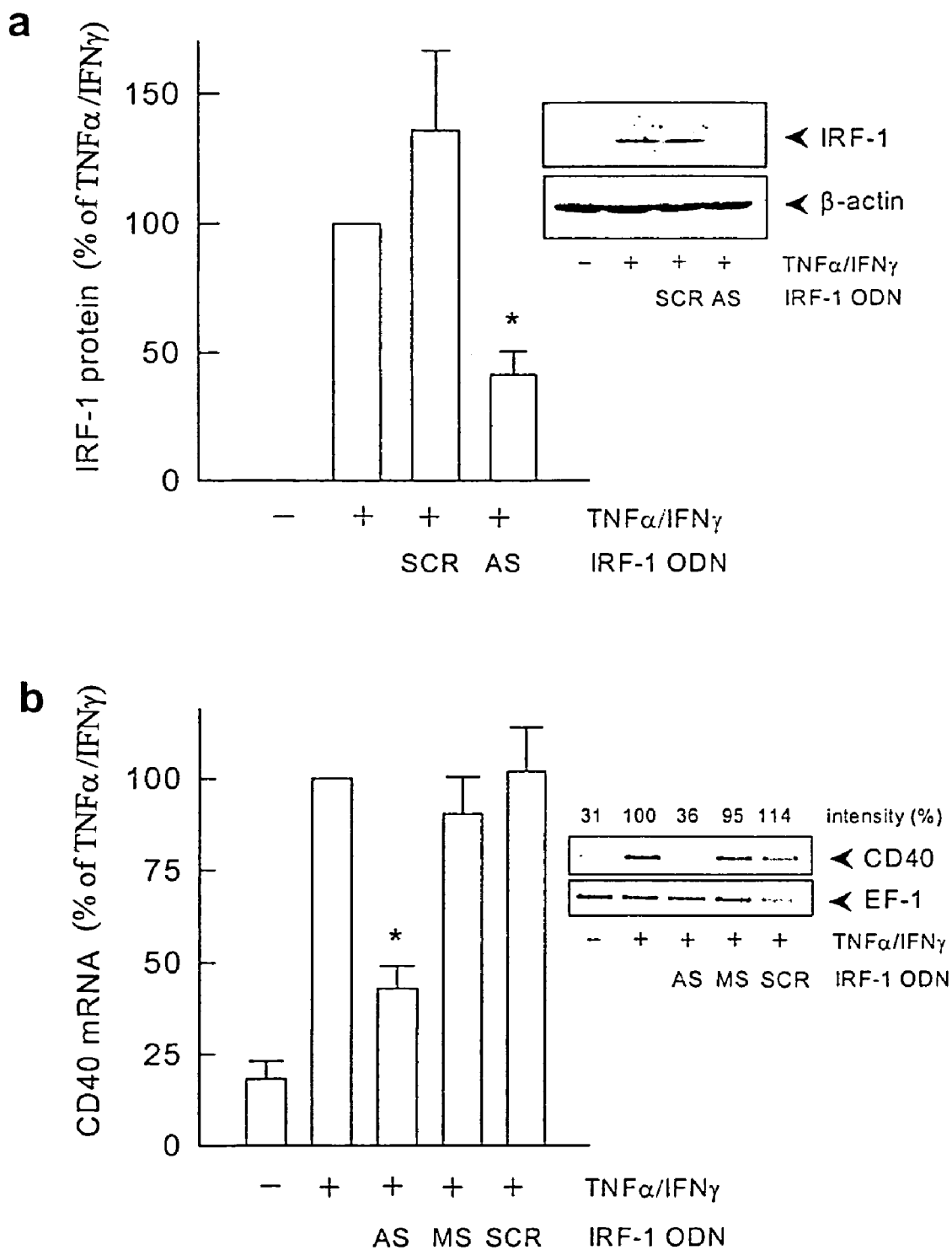

FIG. 8 shows the inhibition of the cytokine induced (100 U/ml) TNFα, (1000 U/ml) IFNγ expression of the IRF-1 protein (after 3 hours) and the CD40 mRNA (after 9 hours) in human endothelium cells which were treated prior for 5 hours with an IRF-1 antisense oligonucleotide (AS; SEQ ID NO:23) (concentration 0.2 μM). The left part of (a) and (b) shows the statistical summary of three experiments with different cell charges, the each right part a representative western blot and RT-PCR analysis, respectively, and in (b) in addition, the densitometrical interpretation ("intensity") given in % of the stimulated control and related to the internal standard β-actin (*P<0.05 compared with the stimulated control cells). The respective missense (MS) and scrambled (SCR), control oligonucleotides respectively influenced neither the expression of IRF-1 nor the expression of CD40.

Figure 9:
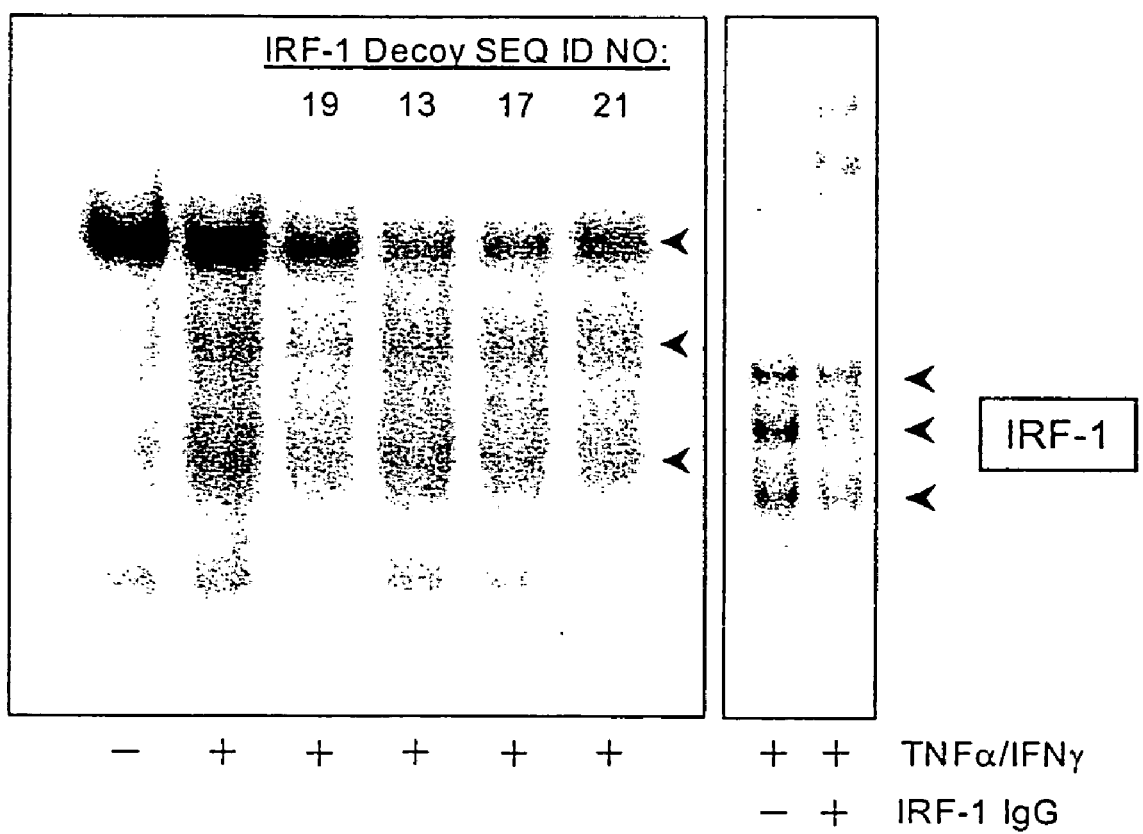

FIG. 9 shows the electrophoretic mobility shift analysis of the uptake of different IRF-1 Cis-element decoys (SEQ ID NO:13, 17, 19 and 21) in cultivated THP-1 cells and the subsequent neutralization of IRF-1. The THP-1 cells were pre-incubated with the different Cis-element decoys for 1 hour and stimulated subsequently for further 3 hours with TNFα (100 U/ml) and IFNγ (1000 U/ml). The result of the following processing and analysis of the samples is shown in the left part of the image. The right part of the image shows the electrophoretic mobility shift analysis of a nuclear extract of stimulated control cells prepared under identical experimental conditions. The nuclear extract was incubated additionally with an anti IRF-1 antibody as described in Krzesz et al. (1999) FEBS Lett. 453, 191 prior to the electrophoretic mobility shift analysis (supershift analysis).

The term "decoy-ODN" or "Cis-element decoy" or "double stranded DNA oligonucleotide" as used herein designates a double stranded DNA molecule, having a sequence corresponding or being similar to the IRF-1 core binding sequence naturally occurring in the genome and to which the transcription factor IRF-1 binds to said sequence in the cell. The Cis-element decoy thus effects as a molecule for the competitive inhibition of IRF-1.

The inventors could solve the transcription factors involved in the inflammation dependent, cytokine mediated increase of the CD40 receptor expression in human endothelium cells. Surprisingly it turned out that the transcription factors Nuclear Factor κB (NFκB) and Signal Transducer and Activator of Transcription-1 (STAT-1) control the tumor necrosis factor α (TNFα)/Interferon-γ (IFNγ)-mediated CD40 expression not in a direct way like in smooth vessel muscle cells of rodents, but in an indirect way by activating of a further transcription factor, namely the Interferon Regulatory Factor-1 (IRF-1). IRF-1 (GenBank Accession No.: L05078, X14454, NM002198 is a transcription factor being not latent present in the cell in contrast to many other transcription factors but needs to be synthesized de novo in fact normally after exposition with Interferon-γ and activation of the transcription factor STAT-1.

In addition Interferonγ stimulates alone or in combination with tumor necrosis factor α in human endothelium cells the expression of CD40. In this contents the TNF-α dependent activation of NFκB plays a minor role. More important is the IFN-γ dependent activation of STAT-1 leading to the de novo expression of IRF-1. IRF-1 then induces the expression of CD40. The synergism of the two cytokines is based essentially on an amplification of the IRF-1 expression. When using the decoy oligonucleotides against STAT-1 and IRF-1 according to the present invention but not the respective control oligonucleotides in human cells in cell culture the cytokine induced CD40 expression (both in monostimulation with IRF-γ and in combination of IFN-γ and TNFα) is inhibited. Thereby the induction of IRF-1 precedes the induction of CD40, so that an antisense oligonucleotide blockade of the IRF-1 expression inhibits the cytokine induced CD40 expression in the same amount as the decoy oligonucleotides. A deactivation of the IRF-1 activity in cells results in a high significant and selective inhibition of the CD40 expression in these cells. As a result of the reduced CD40 expression under pro-inflammatory conditions the endothelium leukocyte interaction particularly the interaction of TH1 and endothelium cells will be toned down and represents the basis for the therapeutical success. The same applies in analogy to reduction of the CD40/CD154 mediated interaction of naive T helper cells with antigen presenting cells (e.g. monocytes, dendritic cells), of TH2 cells with B lymphocytes as well as other CD40 expressing cells (e.g. smooth muscle cells, ceratinocytes, fibroblasts) with CD154 expressing cells (TH1 cells, activated thrombocytes).

One aspect of the present invention refers therefore to the provision of an inhibitor of the activity of the transcription factor IRF-1 as a therapeutical substance. Proteins including also IRF-1 may be inhibited in different ways in their activity. For example anti IRF-1 antibodies, natural or synthetic substances which reduce the IRF-1 interaction with the DNA, i.e. the transactivating activity, may be used. The de novo synthesis of IRF-1 may be further inhibited by blockade of STAT-1 and the signaling path ways (Janus Kinasen) leading to the STAT-1 activating, respectively.

A preferred method to specifically inhibit the IRF-1 activity is the use of double stranded DNA oligonucleotides also named Cis-element decoy or Decoy-ODN having a binding site for IRF-1. The exogenous administration of a large amount of transcription factor binding sites to a cell particularly in a much higher amount as present in the genome leads to a situation in which the majority of a particular transcription factor binds specifically to the respective Cis-element decoy but not to the endogenous target binding sites. This approach to inhibit the binding of transcription factors to their endogenous binding site is also named "squelching". Squelching (also named neutralization) of transcription by use of Cis-element decoys was successfully employed to inhibit the growth of cells. DNA fragments were used thereby comprising the specific transcription factor binding sites of cell transcription factor E2F (Morishita et al., PNAS, (1995) 92, 5855).

The sequence of a nucleic acid used to prevent the binding of the transcription factor IRF-1 is for example a sequence to which IRF-1 binds naturally in the cell. IRF-1 binds specifically to the motive with the sequence 5'-SAAAAGY GAAACC-3' (SEQ ID NO:41), whereby S=C or G and Y=C or T. The binding of IRF-1 depends on the repetitive G/CAAA sequences and the distance between these motives being particularly three nucleotides. Therefore, the Cis-element decoy of the present invention may have the following 13-mer consensus core binding sequence: 5'-SAAAnnnSAAAyy-3' (SEQ ID NO:1), whereby S=C or G, n=A, T, C or G and y=C or T. The Cis-element decoy may further be longer than the 13-mer core binding sequence and may be elongated at the 5'- and/or 3'-terminus. Respective mutations in the core binding sequence result in a loss of the binding of STAT-1 to the decoy oligonucleotide.

As the Cis-element decoy is a double stranded nucleic acid the DNA oligonucleotide according to the present invention comprises not only the sense or the forward sequence, but also the complementary antisense or reverse sequence. Preferred DNA oligonucleotides according to the present invention comprise the following 13-mer core binding sequences for IRF-1:

```
5'-CAAAAGCGAAACC-3',      (SEQ ID NO:3)

5'-GAAAAGCGAAACC-3',      (SEQ ID NO:5)

5'-CAAAAGTGAAACC-3',      (SEQ ID NO:7)

5'-GAAAAGTGAAACC-3',      (SEQ ID NO:9)
``` whereby the respective complementary sequences are not shown. However, the Cis-element decoy may comprise a different sequence to the sequences described above and may be longer than a 13-mer.

The following sequences are more preferred:
(SEQ ID NO:11): 5'-CAGAAAAGTGAAACCCTG-3', 18-mer (not palindromic, 1 binding site),
(SEQ ID NO:13): 5'-CAGTTTCAAATTGAAACTG-3', 19-mer (almost palindromic, 2 binding sites),
(SEQ ID NO:15): 5'-CAGGAAAAGTGAAACCGCTG-3', 20-mer (not palindromic, 1 binding site),
(SEQ ID NO:17): 5'-GCAGTTTCAAATTGAAACTGC-3', 21-mer (almost palindromic, 2 binding sites),
(SEQ ID NO:19): 5'-GGAAGC GAAAATGAAATTGACT-3', 22-mer (primary used consensus-sequence),
(SEQ ID NO:21): 5'-GGCAGTTT CAAATTGAAACTGCC-3', 23-mer (almost palindromic, 2 binding sites).

The wording "2 binding sites" refers to the sense and antisense strand. The listing of the preferred sequences is not limiting. It is obvious for the skilled person that a multitude of sequences may be used as inhibitors for IRF-1 as long as they comprise the conditions listed before of the 13-mer consensus core binding sequence and an affinity to IRF-1.

The affinity of the binding of a nucleic acid sequence to IRF-1 may be determined by the electrophoretic mobility shift assay (EMSA) (Sambrook et al (1989) Molecular Cloning. Cold Spring Harbor Laboratory Press; Krzesz et al. (1999) FEBS Lett. 453, 191). This assay system is suitable for the quality control of nucleic acids which are being used for the method of the present invention or is suitable to determine the optimal length of a binding site. The assay system is also suitable for the identification of further sequences which are being bound by IRF-1. Most suitable for an EMSA which should be used for the isolation of new binding sites are purified or recombinant expressed versions of IRF-1 which are used in several alternating rounds of PCR multiplications and selection by EMSA (Thiesen and Bach (1990) Nucleic Acids Res. 18, 3203).

Genes being known to include IRF-1 binding sites in their promotor or enhancer regions and being therefore putative targets for the specific squelching by the method of the present invention are for example the CD40 gene and further pro-inflammatory genes e.g. cyclooxygenase-2, subunits of the NADPH oxidase (p67phox and gp91phox), the inducible isoform of the nitrogen monoxide (NO)-synthase, the interleukins 6, 8 and 12 as well as the adhesion molecules RANTES (secreted from T lymphocytes in soluble form, regulated upon activation, normal T cell expressed, presumed secreted) and VCAM-1 (vascular cell adhesion molecule-1, named also CD106).

The method of the present invention modulates the transcription of one or more genes in such a way that the gene or the genes, e.g. CD40, are not at all expressed or expressed in a reduced manner. Reduced or inhibited expression in the sense of the present invention means that the transcription rate is reduced in comparison to cells being not treated with the double stranded DNA oligonucleotide according to the present invention. Such a reduction may be determined e.g. by Northern Blotting (Sambrook et al., 1989) or RT-PCR analysis (Sambrook at al., 1989). Such a reduction is typically at least a twofold, preferably at least a fivefold, more preferably at least a tenfold reduction. The loss of activation may be achieved for example when IRF-1 acts as a transcription activator on a certain gene and therefore, this squelching of the activator leads to the loss of expression of the target gene.

In addition the method of the present invention enables the disinhibition of the expression of a gene provided that the expression is blocked by a constitutively active or (after corresponding stimulation of the cell) an activated transcription factor. One example is the disinhibition of the expression of the Prepro-endothelin-1 gene in native rabbit endothelium cells of V. jugularis by a Cis-element decoy against the transcription factor CCAAT/enhancer binding protein (Lauth et al., J. Mol. Med., (2000), 78, 441). The expression of genes the products of which exhibit a protective effect for example against inflammatory diseases may be disinhibited in this way.

The Cis-element decoy used in the present invention includes in a preferred embodiment one or more, preferably 1, 2, 3, 4 or 5, more preferred 1 or 2 binding sites to which IRF-1 specifically binds. The nucleic acids may be generated in synthetically, with enzymatic methods or in cells. The respective methods are state of the art and known to the skilled person.

The length of the double stranded DNA oligonucleotide is at least as long as the used sequence binding specifically to IRF-1. Usually the used double stranded DNA oligonucleotide is between about 13-65 bp, preferably between about 13-26 bp and most preferred between 18-23 bp long.

Usually oligonucleotides are degraded rapidly by endonucleases and exonucleases in particular DNases and RNases in the cell. Therefore, DNA oligonucleotides may be modified to stabilize them against degradation so that a high concentration of the oligonucleotides is maintained in the cell for a longer time. Typically such a stabilization may be achieved by the introduction of one or more modified internucleotide linkages.

A successfully stabilized DNA oligonucleotide contains not necessarily a modification at each internucleotide linkage. Preferably the internucleotide linkages are modified at the respective ends of both oligonucleotides of the Cis-element decoy. The last six, five, four, three, two or the very last or one or more internucleotide linkages within the last six internucleotide linkages may be modified. Furthermore, different modifications of the internucleotide linkages may be introduced into the nucleic acid. The double stranded DNA oligonucleotides generated in this way may be examined for their sequence specific binding to IRF-1 by use of the routine EMSA assay system. This assay system permits the determination of the binding constant of the Cis-element decoy and thus the determination whether the affinity has been changed by way of modification. Modified Cis-element decoys having still a sufficient binding may be selected wherein a sufficient binding stands for at least about 50% or at least about 75% and more preferred about 100% of the binding of an unmodified nucleic acid.

Cis-element decoys with modified internucleotide linkages exhibit still a sufficient binding may be examined whether they are more stable in the cell than the unmodified Cis-element decoys. Cells transfected with Cis-element decoys according to the present invention are examined at different times for the amount of the still existing Cis-element decoys. A Cis-element decoy labeled with a fluorescence dye (e.g. Texas red) or radioactively labeled (e.g. $^{32}$P) is preferably used with a subsequent digital fluorescence microscopy and autoradiography or scintigraphy, respectively. A successfully modified Cis-element decoy exhibits a half life in the cell being higher than the half life of an unmodified Cis-element decoy, preferably of at least about 48 hours, more preferred of at least about four days, most preferred of about at least about seven days.

Suitable modified internucleotide linkages are summarized in Uhlmann and Peyman ((1990) Chem. Rev. 90, 544). Modified internucleotide phosphate moieties and/or non phosphorus bridges in a nucleic acid used in a method of the present invention contain e.g. methyl phosphonate, phosphorothioate, phosphorodithioate, phosphoamidate, phosphate ester, whereas non phosphorus internucleotide analogues contain e.g. siloxane bridges, carbonate bridges, carboxymethylester bridges, acetamidate bridges and/or thioether bridges.

A further embodiment of the invention refers to the stabilization of nucleic acids by introduction of structural features into the nucleic acid which increase the half life of the nucleic acid. Such structures containing the hairpin and bell like DNA are disclosed in U.S. Pat. No. 5,683,985. Modified internucleotide phosphate moieties and/or non phosphorus bridges may be simultaneously introduced together with the above structures. The so generated nucleic acids may be examined with the above described assay system for the binding and stability.

The core binding sequence may not only be present in a Cis-element decoy but also in a vector. In a preferred embodiment the vector is a plasmid vector and more preferred a plasmid vector capable to replicate in an autosomal fashion thereby increasing the stability of the introduced double stranded nucleic acid.

A further aspect of the present invention refers to a double stranded DNA oligonucleotide capable of binding to the transcription factor IRF-1 in a sequence specific manner and having preferably one of the following sequences whereby only one strand of the double stranded DNA oligonucleotide is shown below but the complementary strand is also comprised.

| | |
|---|---|
| 5'-SAAAnnnSAAAyy-3', | (SEQ ID NO:1) |
| 5'-CAAAAGCGAAACC-3', | (SEQ ID NO:3) |
| 5'-GAAAAGCGAAACC-3', | (SEQ ID NO:5) |
| 5'-CAAAAGTGAAACC-3', | (SEQ ID NO:7) |
| 5'-GAAAAGTGAAACC-3', | (SEQ ID NO:9) |
| 5'-CAGAAAAGTGAAACCCTG-3', | (SEQ ID NO:11) |
| 5'-CAGTTTCAAATTGAAACTG-3', | (SEQ ID NO:13) |
| 5'-CAGGAAAAGTGAAACCGCTG-3', | (SEQ ID NO:15) |
| 5'-GCAGTTTCAAATTGAAACTGC-3', | (SEQ ID NO:17) |
| 5'-GGAAGCGAAAATGAAATTGACT-3', | (SEQ ID NO:19) |
| 5'-GGCAGTTTCAAATTGAAACTGCC-3'. | (SEQ ID NO:21) |

Double stranded DNA oligonucleotides of the present invention exhibit a length, modifications and potentially a repeat of the specific binding site as described in detail above. The optimal length of the Cis-element decoy is chosen to optimize the binding to IRF-1 and the uptake into the cell. Usually a double stranded DNA oligonucleotide being shorter than 12 bp binds only in a weak manner to its target protein whereas a double stranded DNA oligonucleotide being longer than 22 bp is taken up by the cell only with low efficiency although it binds in a strong manner. The binding strength may be determined by EMSA whereas the uptake of the double stranded nucleic acid may be analyzed by means of a Cis-element decoy labeled with a fluorescent dye (e.g. Texas red) and radioactively labeled (e.g. $^{32}$P) Cis-element decoy with subsequent digital fluorescent microscopy and autoradiography or scintigraphy, respectively. A Cis-element decoy of the present invention may be stabilized as described above.

A preferred embodiment of the present invention refers to Cis-element decoys containing a palindromic binding site and therefore comprising in a short double stranded nucleic acid at least two transcription factor binding sites. The palindromic sequence does not necessarily entail a higher binding of IRF-1 but said Cis-element decoy will be taken up more rapidly (more efficiently) by the target cells. However, particularly the shorter Cis-element decoys according to the present invention are palindromic only at the ends due to the long (centrally arranged) core binding sequence and the repetitive G/CAAA motives. A preferably similar number of the single basis (A=C=G=T) may be used for a more efficient uptake, however, it is difficult to achieve a more efficient uptake due to the repetitive G/CAAA motive of the Cis-element decoys according to the present invention. A compromise is therefore preferred wherein at least A=T and C=G. Further, preferably the core binding sequence may be arranged rather peripherally as being the case with some of the preferred Cis-element decoy sequences.

A Cis-element decoy according to the present invention is quickly incorporated into the cell. A sufficient uptake is characterized by the modulation of one or more genes which may be modulated by IRF-1. The Cis-element decoy according to the present invention modulates preferably the transcription of one or more genes 4 hours after contact with the cells, more preferred after about 2 hours, after about 1 hour, after about 30 min and most preferred after about 10 min. A mixture usually used in such an experiment contains 10 µmol/L Cis-element decoy.

The present invention further relates to a method to modulate the transcription of a least one gene in CD40 expressing cells, particularly in endothelium cells, monocytes, dentritic cells, B lymphocytes, smooth muscle cells, ceratinocytes or fibroblasts, wherein the method comprises a step of contacting said cells with a mixture, containing one or more double stranded nucleic acids capable of binding to the transcription factor IRF-1 in a sequence specific manner. A preferred method refers to the use in endothelium cells being part of a transplant. The method is usually used at a transplant in vivo or ex vivo prior to the implantation.

The transplants may be treated prior to the implantation by use of the method according to the present invention ex vivo or after implantation by use of the method in vivo. The treated transplant is in a preferred embodiment of (a small) intestine, heart, liver, lung, kidney and pancreas and a combination of several organs, respectively. The treatment of the organs, more precisely the perfusion/incubation of their blood vessels with the Cis-element decoys according to the present invention may occur ex vivo by rinsing the solution immediately prior to the implantation. The organ may be stored simultaneously in a suitable conservation solution (refrigerated) (e.g. University of Wisconsin Solution, Brettschneider HTK solution).

The mixture containing the Cis-element decoys of the present invention is contacted with the target cells (e.g. endothelium cells, monocytes, denditric cells, B lymphocytes, smooth muscle cells, ceratinocytes or fibroblasts). The goal of said contacting is the transfer of the Cis-element decoys binding IRF-1 into the target cell (i.e. the CD40 expressing cell). Therefore, nucleic acid modification and/or additives or adjuvants which are known to increase the penetration of membranes may be used according to the present invention (Uhlmann and Peyman (1990) Chem. Rev. 90, 544).

A mixture according to the present invention contains in a preferred embodiment only nucleic acid and buffer. A suitable concentration of the Cis-element decoys is in the range of at least 0,1 to 100 µmol/L, preferably at 10 µmol/L wherein one or more suitable buffers are added. One example of such buffer is tyrode solution, containing 144.3 mmol/L $Na^+$, 4.0 mmol/L $K^+$, 138.6 mmol/L $Cl^-$, 1.7 mmol/L $Ca^{2+}$, 1.0 mmol/L $Mg^{2+}$, 0.4 mmol/L $HPO_4^{2-}$, 19.9 mmol/L $HCO_3^-$, 10.0 mmol/L D-glucose.

In a further embodiment of the present invention the mixture contains in addition at least one additive and/or adjuvant. Additives and/or adjuvants like lipid, cationic lipids, polymers, liposomes, nanoparticles, nucleic acid aptamers, peptides and proteins being bound to DNA, or synthetic peptide DNA molecules are intended to increase e.g. the incorporation of nucleic acids into the cell, to target the mixture to only one subgroup of cells, to prevent the degradation of the nucleic acid in a cell, to facilitate the storage of the nucleic acid mixture prior to its use. Examples for peptides and proteins are synthetic peptide DNA molecules e.g. antibodies, antibody fragments, ligands, adhesion molecules, which all may be modified or unmodified.

Additives stabilizing the Cis-element decoys in the cell are e.g. nucleic acid condensing substances like cationic polymers, poly L-lysine or polyethyleneimine.

The mixture being used in a method of the present invention is preferably applied locally by injection, catheter, suppository, aerosols (nose and mouth spray, respectively, inhalation), trocars, projectiles, pluronic gels, polymers, which release medicaments permanently, or any other means, which permit local access. Also the ex vivo use of the mixture used in a method of the present invention permits a local access.

The inhibition of the IRF-1 activity may, however, be inhibited not only on protein level in the above described method but may be effected prior or at the translation of the transcription factor protein. A further aspect of the present invention refers, thus, to the provision of an inhibitor of the IRF-1 expression as a therapeutic substance. Said inhibitor is preferably a single stranded nucleic acid molecule, a so called antisense oligonucleotide. Antisense oligonucleotides may inhibit the synthesis of a target gene at three different levels, at the transcription (prevention of the hnRNA synthesis), the processing (splicing) of the hnRNA to mRNA and the translation of the mRNA in protein on the ribosomes. The method to inhibit the expression of genes by antisense oligonucleotides is state of the art and well known to the skilled person. The antisense oligonucleotide against IRF-1 used in the method of the present invention exhibits preferably the sequence 5'-CGAGTGATGGGCATGTTGGC-3' (SEQ ID NO:23) and bridges the start codon. Further preferred sequences of antisense oligonucleotides are 5'-GATTCG-GCTGGTCGC-3' (SEQ ID NO:24), 5'-TAATCCAGAT-GAGCCC-3' (SEQ ID NO:25) and 5'-GGAGCGATTCG-GCTGGT-3' (SEQ ID NO:26). The antisense oligonucleotide may be a single stranded DNA molecule, RNA molecule or a DNA/RNA-hybrid molecule. Further, the antisense oligonucleotide may exhibit one or more modified internucleotide linkages, e.g. the above described sequences of the Cis-element decoy. With an antisense oligonucleotide stabilized by phosphorothioate modified internucleotide linkages it has be preferably to be considered, that between the bases cytosine and guanine no phosphorothioate modified internucleotide linkage is introduced because this results in an IFNγ like activation preferably of immune competent cells (e.g. endothelium cells) and, thus, would foil the desired therapeutic effect at least in part.

A further aspect according to the present invention is an antisense oligonucleotide specifically inhibiting the IRF-1 expression and preferably having one of the following sequences:

```
5'-CGAGTGATGGGCATGTTGGC-3',    (SEQ ID NO:23)
5'-GATTCGGCTGGTCGC-3',         (SEQ ID NO:24)
5'-TAATCCAGATGAGCCC-3',        (SEQ ID NO:25)
5'-GGAGCGATTCGGCTGGT-3'.       (SEQ ID NO:26)
```

A further aspect of the present invention refers further to the use of the antisense oligonucleotides and/or double stranded DNA molecules according to the present invention for the manufacture of a medicament for the prevention and/or therapy of cardiovascular complications like the restenosis after percutan angioplasty or the stenosis of venous bypasses, the chronic (graft arteriosclerosis or vasculopathy) or acute transplant resection, the graft versus host disease (GVAD), immunological hypersensitivity reactions (allergies), particularly bronchial asthma and atopic dermatitis, chronic recurrent inflammation diseases, particularly colitis ulcerosa and Morbus Crohn, psoriasis and sarcoidosis, as well as autoimmune diseases, particularly diabetes mellitus, multiple sclerosis, collagenosis (for example systemic Lupus erythematodes), rheumatoid arthritis and vasculotids. A particular advantage of this therapeutic approach further consists of the simultaneous reduction of the TH1- and TH2-cell-response to which the CD40/CD154 signalling pathway effects co-stimulatorily. Thereby it could not lead to a disinhibition of the TH1 cell reaction (for example psoriasis) with attenuation of the TH2 cell reaction (e.g. atopic dermatitis) and vice versa, respectively.

The following examples and figures explain the invention but are not intended to limit the scope of the invention.

1. Cell Culture

Human endothelium cells were isolated from umbilical veins by treating with 1.6 U/ml dispase in hepes modified tyrode solution for 30 min by 37° C. The cells were cultivated on 6 well tissue cultures coated with gelatin (2 mg/ml gelatin in 0.1 M HCl for 30 min at room temperature; RT) in 1.5 ml M199 medium containing 20% fetal calf serum, 50 U/ml penicillin, 50 µg/ml streptomycin, 10 U/ml nystatin, 5 mM HEPES and 5 mM TES, 1 µg/ml heparin and 40 µg/ml endothelial growth factor. The cells were identified by their typical paving stone morphology, positive immunostaining for the von Willebrandt-Factor (vWF) and fluorimetric detection (FACS) of PECAM-1 (CD31) as well as negative immunostaining for smooth muscle α-Actin (Krzesz at al. (1999) FEBS Lett. 453, 191).

2. RT-PCR Analysis

The endothelial total RNA was isolated with the Qiagen RNeasy Kit (Qiagen, Hilden, Germany) with a subsequent cDNA Synthesis with the maximum of 3 µg RNA and 200 U Superscript™ II reverse transcriptase (Gibco Life Technologies, Karlsruhe, Germany) in a total volume of 20 µl according to the manufactorer's instructions. To adjust the cDNA load 5 µl (approximately 75 ng cDNA) of the resulting cDNA solution and the primer pair (Gibco) for the elongation factor 1 (EF-1) PCR with 1 U Taq DNA polymerase (Gibco) was used in a total volume of 50 µl. EF-1 was used as internal Standard for the PCR. The PCR products were separated on 1.5% agarose gels containing 0.1% ethidiumbromide and the intensities of the bands were determined densitometrically with a CCD camera system and the One Dscan Gel Analysis Software from Scanalytics (Billerica, Mass., USA) to adjust the volume of the cDNA in subsequent PCR analyses.

All PCR reactions were individually performed for each primer pair in a Hybaid OmnE Thermocycler (AWG, Heidelberg, Germany). The individual PCR conditions for the cDNA of human endothelial umbilical veins were as follows: CD40 (amplicon size 381 bp, 25 cycles, annealing temperature 60° C., (forward primer) 5'-CAGAGTTCACT-GAAACGGAATGCC-3' (SEQ ID NO:27), (reverse primer) 5'-TGCCTGCCTGTTGCACAACC-3' (SEQ ID NO:28); E-Selectin (amplicon size 304 bp, 33 cycles, annealing temperature 60° C., (forward primer) 5'-AGCAAGGCATGAT-GTTAACC-3' (SEQ ID NO:29), (reverse primer) 5'-GCAT-TCCTCTCTTCCAGAGC-3' (SEQ ID NO:30); IRF-1 (amplicon size 310 bp, 29 cycles, annealing temperature 55° C., (forward primer) 5'-TTCCCTCTTCCACTCGGAGT-3' (SEQ ID NO:31), (reverse primer) 5'-GATATCTGGCAGG-GAGTTCA-3' (SEQ ID NO:32); EF-1 (amplicon size 220 bp, 22 cycles, annealing temperature 55° C., (forward primer) 5'-TCTTAATCAGTGGTGGAAG-3' (SEQ ID NO:33), (reverse primer) 5'-TTTGGTCAAGTTGTTTCC-3' (SEQ ID NO:34).

3. Electrophoretic Mobility Shift Analysis (EMSA)

The nuclear extracts and [$^{32}$P]-labeled double stranded consensus oligonucleotides (Santa Cruz Biotechnologie, Heidelberg, Germany) non denaturing polyacrylamidgelelectrophoreses, autoradiographie and supershift analysis were performed as described by Krzesz at al (1999) FEBS Lett. 453, 191. Oligonucleotides were used with the following single stranded sequences (core binding sequences are underlined): NFκB, 5'-AGTTGA<u>GGGGACTTTCCC</u>AGGC-3' (SEQ ID NO:35); STAT-1, 5'-CATGTTATG<u>CATATTCCTGTAAGT</u> G-3' (SEQ ID NO:36); IRF-1, 5'-GGAAGC<u>GAAAATGAAATT</u>GACT-3' (SEQ ID NO:19).

4. Decoy Oligonucleotide (dODN) Technique

Double stranded dODNs were generated from the complementary single stranded phosphorothioate linked oligonucleotides (Eurogentec, Cologne, Germany) as described by Krzesz et al. (1999) FEBS Lett. 453, 191. The cultivated human endothelium cells were pre-incubated for 4 hours with a concentration of 10 µM of the respective dODN. These were the same conditions which have been optimized previously due to EMSA and RT-PCR analyses. The dODN containing medium was usually replaced afterwards with fresh medium. The single stranded sequences of the dODNs are set forth below (underlined letters designate phosphorithioate linked bases, all sequences are written in 5'-3' direction):

```
NTkB,       AGTTGAGGGGACTTTCCCAGGC;      (SEQ ID NO:35)
STAT-1,     CATGTTATGCATATTCCTGTAAGTG;   (SEQ ID NO:36)
IRF-1,      GGAAGCGAAAATGAAATTGACT;      (SEQ ID NO:19)
IRF-1n      CAGAAAAGTGAAACCCTG;          (SEQ ID NO:11)
cons
IRF-1n      CAGATGAGTGTAACCCTG.          (SEQ ID NO:37)
mut
```

5. Antisense Oligonucleotide Technique

3% Lipofectin (v/v) (Gibco Life Technologies, Karlsruhe, Germany) was added to 1 ml culture medium for an antisense experiment and was incubated for 30 min at room temperature. The respective antisense oligonucleotide (Eurogentec, Cologne, Germany) was subsequently added in a final concentration of 0.2 μM and incubated for further 15 min at room temperature. At the beginning of the experiment the respective amounts of Heparin and endothelial growth factor were added and the conventional cell culture medium of the endothelium cell culture was replaced by antisense Lipofectin Medium. The antisense Lipofectin Medium was removed after 5 hours and replaced by fresh cell culture medium. The sequence of the IRF-1 antisense oligonucleotide (IRF-1 AS) was 5'-CGAGTGATGGGCATGTTGGC-3' (SEQ ID NO:23). A missense oligonucleotide (IRF-1 MS, 5'-CGAGTGGTAGACGTATTGGC-3' (SEQ ID NO: 38)) and a scrambled oligonucleotide (IRF-1 SCR, 5'-GAGCT-GCTGAGGTCGTTGAG-3' (SEQ ID NO:39)) were used as control oligos.

6. Fluorescence Activated Cell Sorting (FACS)

The endothelium cells to be analyzed were washed initially three times with 1 ml FACS buffer (PBS, 2% fetal calf serum sterile filtrated) each resuspended subsequently in 2 ml FACS buffer. The fluorescence labeled antibody (Pharmingen, San Diego, USA) was added according to the instructions of the manufacturer (20 μl/$10^6$ cells) after centrifugation (300×g, 5 min, +4° C.) and determination of the total cell number (Neubauer Counting Chamber) and incubated for 30 min at +4° C. in the dark. The sample was subsequently washed with 2 ml FACS buffer and centrifuged for 10 min at 300×g and +4° C. The supernatant was removed and the cell pellet was resuspended in 1 ml Cell Fix (PBS, 1% formaldehyde) and stored in the dark until measuring at +4° C. (EPICS®XL MCL, Coulter, Krefeld, Germany). The following antibodies were used: CD40, R-Phycoerythrin (RPE)- and Fluorescein Isothiocyanate (FITC)-conjugated; PECAM-1 (CD31), Fluorescein Isothiocyanate (FITC)-conjugated. The respective RPE- and FITC-conjugated isotype controls were used to determine unspecific cell antibody bindings.

7. Western Blot Analysis

The endothelium cells were macerated by 5 consecutive freeze thaw cycles in liquid nitrogen and 37° C. (heating block, Kleinfelden, Germany). Protein extracts were generated as described by Hecker et al. (1994) Biochem J 299, 247. 20-30 μg Protein were separated with a 10% polyacrylamide-gelelectrophoresis under denaturing conditions in the presence of SDS according to a standard protocol and transferred to a BioTrace™ Polyvinylidene Fluoride Transfermembran (Pall Corporation, Roβdorf, Germany). A polyclonal primary antibody directed against the C-terminus of the CD40 protein (Research Diagnostics Inc., Flanders, N.J., USA) was used to detect the CD40 protein. The protein bands were detected after adding a peroxidase coupled anti rabbit IgG (1:3000, Sigma, Deisenhofen, Germany) by means of a chemiluminescent method (SuperSignal Chemiluminescent Substrat; Pierce Chemical, Rockford, Ill., USA) coupled with a subsequent autoradiography (Hyperfilm™ MP, Amersham Pharmacia Biotech, Buckinghamshire, GB). The loading and transfer of identical protein amounts was shown by staining of the blot with blue ink.

8. Statistical Analysis

Unless shown differently all data in figures and in the text are shown as mean±SD of n experiments. The statistical analysis was performed with the Students t-Test for unpaired data with a p-value<0.05, which was taken as statistically significant.

9. Experimental Proof on Animals of the CD40/CD154 Associated Transplant Rejection The transplant rejection in rats was examined experimentally on animals by use of a STAT-1 decoy oligonucleotide because STAT-1 is responsible in rats for the Interferon-γ induced CD40 expression rather than of IRF-1 as in humans (Krzesz et al. (1999) FEBS Lett. 453, 191).

Strain Combination

The strain combination Brown Norway donor was used for the allogenic transplantation to Lewis recipients. Without an immunosuppression the transplant was rejected after 7 days. The transplantation from Lewis to Lewis war performed as syngenic control.

Explantation

The abdomen of an animal was opened in the mid line under ether inhalation narcosis. An aorta segment was first released from all arterial parts so that approximately a 1 cm long aortic segment with prospective Ateria mesenterica was prepared. The complete colon was removed in the next step. Thereafter all venous vessels of the portal vein were ligated in the latitude of the pancreas so that the pancreas was unrestrained into the porta hepatis. The so prepared donor small intestine was now attached only to the trunc of the aorta and the portal vein. The aorta was clamped proximal and distal of the ateria mesenterica, the portal vein was severed at the porta hepatis and the vascular bed of the small intestine was rinsed with cold University of Wisconsin (UW) solution until no macroscopic blood residues were left in the vascular bed. The intestine lumen was likewise rinsed in the last step with cold UW solution, the intestine with an aorta segment was taken off and stored in cold UW solution until implantation occurred (up to 120 min). When the transplant was treated with the STAT-1 Decoy Oligonucleotide (sequence: CATGT-TATGCATATTCCTGTAAGTG; (SEQ ID NO:36)) or the respective mutated control nucleotide (sequence: CATGT-TATGCAGACCGTAGTAAGTG (SEQ ID NO:40)), the transplant was infused into the arteria mesenterica in Ringer solution (containing 145 mmol/L $Na^+$, 5 mmol/L $K^+$, 156 mmol/L $Cl^-$, 2 mmol/L $Ca^{2+}$, 1 mmol/L $Mg^{2+}$, 10 mmol/L Hepes, 10 mmol/L D-glucose, pH 7,4; volume 3 ml, final concentration 20 μmol/L) and rinsed with Ringer solution immediately before the anastomorization.

Implantation

The abdomen of an animal was opened in the mid line in ether inhalation narcosis. The aorta and vena cava were prepared and clamped simultaneously. Vessel connection was done in end-to-side in an continuing suture technique with a 8-0 nylon stitch. The ateria mesenterica carrying the aorta segment was anastomosed at the infravenal aorta and the portal vein was anastomosed at the infravenal vena cava. After release of the circulation the terminal ileum of the donor intestine was connected end-to-side to the terminal ileum of the donor intestine also by a 6-0 nylon stitch. The mucus produced by the donor intestine was drained off into the normal passage of the animal. The oral end of the donor intestine was closed by ligature and the abdomen was continuously disclosed in a two layer fashion. The animals receive postoperatively for analgesia reasons Temgesic into their drinking water.

Intravital Microscopie

An assessment of the importance of the leucocyte endothelium interaction for the inflammation reaction was possible only by intravital microscopy analysis. This method enabled an observation of the "rolling and adhering" of leucocytes at the endothelium in vivo as well as an quantitative analysis of micro vascular parameters (perfusion of the tissue, functional capillary density and blood flow).

The intravital microscopy was performed with a Axiotech Vario 100 microscope from Zeiss (Göttingen) endowed with a HBO 100 mercury lamp for epifluorescence measurements. With the 10×, 20× and 40× (water immersions) lenses a solution of 243×, 476× and 933× was achieved. The microscopic images were taken with a CCD video camera (CF 8/1, Kappa) and stored for analysis on a video tape.

The rats (6 animals per group) were examined 7 days after the transplantation in deep diethylether narcosis with intravital microscopy. To facilitate the breathing the trachea was cannulated. A polyurethane catheter was positioned into the arteria carotis for permanent monitoring of the blood pressure for the simplification of the application of dyes. The body temperature of the animals was held constant with a heatable plate. The animals were opened by a ventral median cut, the colon descendens was evacuated, a small cut was set anti mesenterially and the intestine was fixed in a specific fixture to facilitate the microscopy. To prevent a drying of the tissue, the intestine was moistened permanently with Ringer solution. The intestine microcirculation was made visible by the injection of 0.8 ml 0.5% FITC (fluorescein isothiacyanate) coupled dextrane. To cover the measurements statistically a least ten different areas of the respective intestine part was examined. The different parameters were quantified as follows: The perfusion index resulted from the perfused mucosa areas (in %)+0.5 × of all irregularly perfused mucosa areas (in %). The functional capillary density was determined by a computer aided image analysis (CAP-IMAGE software, Zeintl, Heidelberg, Germany). To examine the leukocyte endothelial interactions the leukocytes were labeled by the injection of 0.2 ml 0.1% Rhodamine-6 G (Sigma, Heidelberg, Germany) and the post capillary venoles were microscoped in the submucosa. Those leukocytes were defined as adherent leukocytes ("sticker") which attached to a vessel segment 100 µm length for at least 20 sec at the endothelium. The number of the sticker number/mm$^2$ endothelium surface was calculated. The endothelium surface resulted from the surface calculation for a cylinder.

Results of the Small Intestine Transplantation

The mucosal functional capillary density as a unit of measurement of the perfusion, was reduced down to 10% of the values of syngenic transplanted small intestines both in the control group and in the group treated with the mutated control oligonucleotides without rejection. The functional capillary density was increased four times in contrast in small intestines treated with the STAT-1 Cis-element decoy. The blood flow (flow rate of the erythrocytes) was in these animals 10 times higher and the perfusion index was 3 times higher. The staseindex was reduced for 60% and the number of the leucocytes attached to the endothelium was reduced for 25%. Only the latter parameter was not statistically significant altered. The rejection induced reduction of the intestine perfusion and thus, the degeneration of the transplant was in summary significantly reduced in the group treated with the Cis-element decoy.

The invention claimed is:

1. An inhibitor of IRF-1 activity, wherein the inhibitor is a double-stranded DNA molecule having a length of 18 to 23 base pairs and comprising the sequence of SEQ ID NO:11 in one strand and SEQ ID NO:12 in the complementary strand.

2. The inhibitor according to claim 1, wherein the double-stranded DNA molecule comprises modified internucleotide linkages.

* * * * *

UNITED STATES PATENT AND TRADEMARK OFFICE
CERTIFICATE OF CORRECTION

| | | |
|---|---|---|
| PATENT NO. | : 7,524,949 B2 | Page 1 of 1 |
| APPLICATION NO. | : 10/398592 | |
| DATED | : April 28, 2009 | |
| INVENTOR(S) | : Markus Hecker et al. | |

It is certified that error appears in the above-identified patent and that said Letters Patent is hereby corrected as shown below:

In title page, item (30) Foreign Application Priority Data, insert:
--October 6, 2000       (DE) .......... 100 49 549
  November 29, 2000     (DE) .......... 100 59 144--.

Signed and Sealed this

Eleventh Day of August, 2009

David J. Kappos
*Director of the United States Patent and Trademark Office*

SEQUENCE LISTING

```
<160> NUMBER OF SEQ ID NOS: 40

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (5)..(7)
<223> OTHER INFORMATION: N = A, C, G or T/U

<400> SEQUENCE: 1
saaannnsaa ayy                                                           13

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (7)..(9)
<223> OTHER INFORMATION: N = A, C, G or T/U

<400> SEQUENCE: 2
yytttsnnnt tts                                                           13

<210> SEQ ID NO 3
<211> LENGTH: 13
<212> TYPE: DNA
```

```
<213> ORGANISM: Artificial Sequence
<220> FEATURE:
<223> OTHER INFORMATION: Description of Artificial Sequence: Synthetic
      Primer

<400> SEQUENCE: 3
caaaagcgaa acc                                                         13

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
ggtttcgctt ttg                                                         13

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
gaaaagcgaa acc                                                         13

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
ggtttcgctt ttc                                                         13

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
caaaagtgaa acc                                                         13

<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
ggtttcactt ttg                                                         13

<210> SEQ ID NO 9
<211> LENGTH: 13
<212> TYPE: DNA
<213> ORGANISM: Artificial Sequence
```

-continued

```
<220> FEATURE:
<223> OTHER INFORMATION: Description of Artificial Sequence: Synthetic
      Primer

<400> SEQUENCE: 9
gaaaagtgaa acc                                                              13

<210> SEQ ID NO 10
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
ggtttcactt ttc                                                              13

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
cagaaaagtg aaaccctg                                                         18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
cagggtttca cttttctg                                                         18

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
cagtttcaaa ttgaaactg                                                        19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
cagtttcaat ttgaaactg                                                        19

<210> SEQ ID NO 15
<211> LENGTH: 20
<212> TYPE: DNA
<213> ORGANISM: Artificial Sequence
<220> FEATURE:
```

<223> OTHER INFORMATION: Description of Artificial Sequence: Synthetic
      Primer

<400> SEQUENCE: 15
caggaaaagt gaaaccgctg                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
cagcggtttc acttttcctg                                                    20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
gcagtttcaa attgaaactg c                                                  21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
gcagtttcaa tttgaaactg c                                                  21

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
ggaagcgaaa atgaaattga ct                                                 22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
agtcaatttc attttcgctt cc                                                 22

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic

```
          Primer

<400> SEQUENCE: 21
ggcagtttca aattgaaact gcc                                          23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 22
ggcagtttca atttgaaact gcc                                          23

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 23
cgagtgatgg gcatgttggc                                              20

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 24
gattcggctg gtcgc                                                   15

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 25
taatccagat gagccc                                                  16

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 26
ggagcgattc ggctggt                                                 17

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer
```

```
<400> SEQUENCE: 27
cagagttcac tgaaacggaa tgcc                                           24

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
tgcctgcctg ttgcacaacc                                                20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
agcaaggcat gatgttaacc                                                20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
gcattcctct cttccagagc                                                20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
ttccctcttc cactcggagt                                                20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
gatatctggc agggagttca                                                20

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer
```

<400> SEQUENCE: 33
tcttaatcag tggtggaag         19

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
tttggtcaag ttgtttcc         18

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
agttgagggg actttcccag gc         22

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
catgttatgc atattcctgt aagt         24

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
cagatgagtg taaccctg         18

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
cgagtggtag acgtattggc         20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39

```
gagctgctga ggtcgttgag                                              20

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 40
catgttatgc agaccgtagt aagtg                                        25
```